(12) United States Patent
Ja

(10) Patent No.: US 7,835,006 B2
(45) Date of Patent: Nov. 16, 2010

(54) OPTICAL FIBER SENSORS USING GRATING-ASSISTED SURFACE PLASMON-COUPLED EMISSION (GASPCE)

(75) Inventor: Shiou-jyh Ja, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 152 days.

(21) Appl. No.: 11/267,093

(22) Filed: Nov. 4, 2005

(65) Prior Publication Data

US 2008/0007732 A1    Jan. 10, 2008

Related U.S. Application Data

(60) Provisional application No. 60/625,663, filed on Nov. 5, 2004.

(51) Int. Cl.
*G01B 11/06* (2006.01)
(52) U.S. Cl. .................. 356/445; 435/288.7; 436/165; 250/227.24
(58) Field of Classification Search .................. 356/445
See application file for complete search history.

(56) References Cited

U.S. PATENT DOCUMENTS

| | | | |
|---|---|---|---|
| 5,260,854 A | 11/1993 | Hileman et al. | |
| 5,442,448 A * | 8/1995 | Knoll | 356/445 |
| 6,331,079 B1 | 12/2001 | Grois et al. | |
| 6,361,218 B1 | 3/2002 | Matasck et al. | |
| 6,371,657 B1 | 4/2002 | Chen et al. | |
| 6,642,881 B1 * | 11/2003 | Lawrence et al. | 342/4 |
| 6,811,322 B2 | 11/2004 | Chen et al. | |
| 6,976,303 B2 | 12/2005 | Chen et al. | |
| 6,981,803 B2 | 1/2006 | Grzegorzewska et al. | |
| 2002/0135312 A1 * | 9/2002 | Koyama | 315/169.3 |
| 2004/0170371 A1 * | 9/2004 | Arkhipov et al. | 385/141 |
| 2005/0036140 A1 * | 2/2005 | Elster et al. | 356/246 |

(Continued)

FOREIGN PATENT DOCUMENTS

WO    WO 98/25313    * 6/1998

(Continued)

OTHER PUBLICATIONS

Gifford, Dawn K and Dennis G. Hall, "Emission through one of two metal electrodes of an organice light-emitting diode via surface-plasmon cross coupling", Applied Physics Letters vol. 81, No. 23, Dec. 2, 2002, pp. 4315-4317.*

(Continued)

*Primary Examiner*—Gregory J Toatley, Jr.
*Assistant Examiner*—Rebecca C Slomski
(74) *Attorney, Agent, or Firm*—Dunlap Codding, P.C.

(57) ABSTRACT

The present invention relates to a new fluorescence detection platform based on the integration of grating-assisted surface plasmon coupled emission (GASPCE). This innovation builds upon the traditional SPCE technique by adding a grating to the metal surface which thereby provides additional emission confinement. The original conical emission pattern associated with the traditional SPCE technique is "squeezed" into a "two-beam" emission pattern that is more readily interrogated and collected by a waveguiding structure. With the GASPCE method and system of the present invention, a fluorescence emission can be coupled into optical waveguide with greater efficiency. As such, the integration of the GASPCE and existing optical fiber networking offers distributed real-time sensing capabilities. Also, the integration with an integrated optical chip may enable multi-channel array sensing or high-throughput florescence sensing.

14 Claims, 10 Drawing Sheets

U.S. PATENT DOCUMENTS

2005/0053974 A1* 3/2005 Lakowicz et al. .............. 435/6
2005/0088084 A1* 4/2005 Cok ........................... 313/506
2006/0194346 A1* 8/2006 Knoll et al. ................. 436/525

OTHER PUBLICATIONS

Hobson, Peter A. et al. "Surface Plasmon Mediated Emission from Organice Light-Emitting Diodes", Advanced Materials 2002, 14, No. 19, Oct. 2, pp. 1393-1396.*

"Energy Transfer From an Excited Dye Molecule to the Surface Plasmons of an Adjacent Metal", W. H. Weber and C. F. Eagen, Optics Letters, 4, pages 236-238, 1979.

"Electromagnetic Interactions of Molecules with Metal Surfaces", G. W. Ford and W. H. Weber, Physics Reports, 113, pp. 195-287, 1984.

"Radative Decay Engineering 3. Surface Plasmon-Coupled Directional Emission", J. R. Lakowicz, Analytical Biochemistry, 324, pp. 153-169, 2004.

"Radiative Decay Engineering 4. Experimental Studies of Surface Plasmon-Coupled Directional Emission", I. Gryczynski, J. Malicka, Z. Gryczynski, and J. R. Lakowicz; Analytical Biochemistry, 324, pp. 170-182; 2004.

"Forbidden Light Detection from Single Molecules", T. Ruckstuhl, J. Enderlein, S. Jung, and S. Seeger; Analytical Chemistry; 72, pp. 2117-2123; 2000.

"Highly Efficient Optical Detection of Surface-Generated Fluorescence", J. Enderlein, T. Ruckstuhl, S. Seeger; Applied Optics, 38; pp. 724-732, 1999.

"Single-Molecule Fluorescence Near a Metal Layer", J. Enderlein; 247, pp. 1-9; 1999.

"Transmission of Molecular Fluorescence Through a Thin Metal Film by Surface Plasmon", R. W. Gruhlke and D. G. Hall, Applied Physics Letters, 53; 1041-1042;1988.

"Photoluminescense from Dye Molecules on Silver Gratings", S. C. Kitson, W. L. Barnes, and J. R. Samples; Optics Communications, 12, pp. 147-154; 1996.

"Surface Plasmon Resonance Studies of Immunoreactions Utilizing Disposable Diffraction Gratings", C. R. Lawrence, N. J. Geddes, and D. N. Furlong; Biosensors and Bioelectronics, 11, pp. 389-400; 1996.

"Value Proposition", LittleOptics, Inc., pp. 1-8; website: http://www.littleoptics.com.

* cited by examiner

OPTICAL FIBER SENSORS USING GRATING-ASSISTED SURFACE PLASMON-COUPLED EMISSION (GASPCE)

CROSS-REFERENCE TO RELATED APPLICATIONS

The present patent application claims priority under 35 U.S.C. §119(e) to the U.S. provisional patent application identified by U.S. Ser. No. 60/625,663, filed Nov. 5, 2004 entitled "OPTICAL FIBER SENSORS USING GRATING-ASSISTED SURFACE PLASMON-COUPLED EMISSION (GASPCE)", the entire content of which is hereby expressly incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to a fluorescence detection platform, and more particularly, but not by way of limitation, to a fluorescence detection platform based on the integration of grating-assisted surface plasmon coupled emission.

2. Description of the Prior Art

The phenomenon known as surface plasmon-coupled emission (SPCE) involves the coupling of surface plasmon resonance (SPR) and nearby spontaneous emission. Since the observance of SPCE in 1975, an abundance of literature containing both experimental and theoretical works has been recorded. It has been shown that, for example, the fluorescence of molecules nearby a metal film can be coupled into the surface plasmon (SP) mode, re-radiated out penetrating through the metal film into a higher refractive index substrate, and then focused at a well-defined angle. This angle generally corresponds to the "minimum total reflection angle", which is often used to generate SPR in the Kretschmann configuration (i.e., the SPCE emission angle is the same as the SPR excitation angle with the same wavelength). Since there is a one-dimensional confinement applied to the emission, the SPCE radiation pattern is a cone 10, as shown for example in FIG. 1.

Various experiments demonstrating SPCE have been conducted. An example of an experiment setup conducted by Weber is shown above in FIGS. 1 and 2. The experiment setup includes a rhodamine-methanol solution 12 excited by a p-polarized Ar laser (514.5 nm) through a high refractive index prism 14 and a 75-nm thick Ag film 16. Since the transmission spectral bandwidth of the emission through a filter 17 is broad, the range of the corresponding SP angle is also large, and the emission cone 10 has a thick width. When this emission cone 10 is projected onto a linear photograph plate 18, a wide band is shown. If a color film is used for the same experiment, it will show rainbow-like color bands. This is essentially an "SPR grating", which emits light of different colors into different angles.

The SPR grating effect and the preferential emission of SPCE through metal thin film into the high refractive index (prism) side can be understood by the wavenumber (also known as the propagation constant or momentum) matching criteria:

$$k_0 n_p \sin \theta_f = \text{Re}[k_{sp}], \quad (1)$$

where $k_0$, $k_{sp}$, $n_p$, and $\theta_f$ are the free-space wavenumber, SP wavenumber, refractive index of the prism, and SPCE emission angle, respectively. As the SP wavenumber, $$k_{sp} = k_0 \sqrt{\frac{\varepsilon_m \varepsilon_s}{\varepsilon_m + \varepsilon_s}}$$

(where $\varepsilon_m$, $\varepsilon_s$ are the permittivities of the metal and sample solution), changes at different emission wavelength due to the material dispersion, the emission angle shifts correspondently.

SPCE can be modeled as a dipole emitter located in the proximity of a metal structure. In particular, FIG. 3 shows a SPCE emission pattern numerically simulated by using the two-dimensional (2D) finite difference time domain (FDTD) method. Black vertical lines 20 indicate the boundaries of the metal layer. To the left side of the black vertical lines 20 is free space 22, and the right side is filled with high refractive index material 24 (e.g., glass). A dipole normal to the metal surface emits preferentially to the high refractive index side at the SPR excitation angle.

The potential applications of SPCE are significant since any spontaneous emission process, such as fluorescence, fluorescence resonance energy transfer (FRET), Raman scattering, second harmonic generation (SHG), etc., may take advantage of the SPCE phenomenon. More particularly for fluorescence-related sensing applications, the use of SPCE offers several interesting and highly desirable features. Such features include:

Highly efficient fluorescence collection
Background noise reduction
Fluorescence intensity enhancement
Photostability improvement Generally, due to the isotropic emission pattern of fluorescence, the common spontaneous emission collection efficiency is about 1%. However, the SPCE has an emission pattern that essentially focuses itself into a narrower spatial distribution. Although, only the vertically oriented dipole has a high probability of SPCE coupling. As such, the averaging effect (among vertical and horizontal orientation) dilutes the maximum harvest efficiency of the traditional SPCE technique to about 50-60%. This emission confinement not only improves the signal collection efficiency, but also reduces background noise due to reduced data collection volume, near-field coupling, and possible polarization discrimination.

SPCE is categorized as the so-called "forbidden light" 30 detection scheme. When ambient light 32 enters a higher-refractive-index material 34, the transmitted light is only allowed to go into a transmission angle 36 smaller than the critical angle 38. As shown in FIG. 4, no other light besides the emission originated at the proximity of the material interface can be coupled into the forbidden region 30 (i.e., the transmission angle is greater than the critical angle). Therefore, forbidden light 31 has ultra-high signal to noise ratio (SNR) due to the very dark background and only the presence of the dipole radiation close to the interface (which is the intended signal). Since a major portion of the SPCE is focused into an emission angle 40 greater than the critical angle 38, SPCE is an excellent candidate for the forbidden light detection scheme. In addition, SPCE light is p-polarized with great polarization purity, which enables further boosting of SNR via polarization filtering.

The effect on the emission of presenting a metal surface to fluorescencing molecules can be quite different depending on the newly created photonic mode density (PMD). The presence of metal can introduce a new pathway or alter the existing mechanism of the decay processes, which may either boost the radiative rate and hence fluorescence enhancement, or promote non-radiative decay and hence fluorescence quenching. Many theoretical works have been conducted to understand this behavior.

Fluorescence is a radiative decay process, which competes with several other nonradiative decay mechanisms. It is well known that the radiative decay can be engineered by the surrounding PMD. The spontaneous emission usually interacts with the PMD via the evanescent field (near field). Enderlein has conducted some theoretical studies about such effect by modeling it as the dipole-interface interaction using the semi-classical electromagnetic theory. The modification of FRET due to the changing PMD can also be modeled as the resonance dipole-dipole interaction (RDDI) using a similar approach. However, the evanescent field generated near the noble metal surface via SPR is stronger and extends farther than the one near the dielectric interface via total internal refection (TIR). Therefore, the modification of the emission due to SPR is more dramatic than its counterpart produced by refractive index contrast. This fact grants SPCE, which utilizes SPR, a stronger improvement over other techniques of coupling spontaneous emissions.

The fluorescence intensity enhancement of SPCE comes from several factors. First, the excitation may be locally amplified via the SPR enhancement. Secondly, the radiative lifetime may be reduced due to the change of the PMD around the emitter, and hence the quantum yield efficiency is increased. Finally, the non-radiative decay is reduced in the competitive process, which results in less damage onto fluorescencing molecules and improves photostability.

The probability of the SP-coupled radiative decay rate has been calculated by Weber in 1979. FIG. 5 shows that the probability SPCE can be as high as 93% when the fluorescing molecule is vertically oriented and 120-nm away from the metal surface. However, the horizontally oriented molecule has much lower SPCE coupling probability under the same condition. In an orientation-randomized scenario, the averaged SPCE is presented as a dashed line in FIG. 5.

Ford et al. also published similar calculations in 1984. FIG. 6 presents the relative decay probability of both non-radiative and radiative mechanisms. It can be seen that the non-radiative decay (dotted lines) dominates when the molecule-metal separation is under 10-nm for both vertically ($\perp$) and horizontally ($\parallel$) oriented molecules. As the separation increases, the SPCE-related decay (solid lines) rises up quickly for the vertically oriented molecule, but not for the horizontal one.

The SPCE coupling range can be rather long such that it actually peaks at around 120 nm, which agrees well with Weber's results. The free-space non-SPCE related radiative decay also has been presented as dashed lines in FIG. 6. At about 120-nm away from metal surface, the free-space radiative decay actually dominates for the horizontally oriented molecules. Therefore, the preferential emission characteristic is "diluted" in the orientation-randomized case. Both works discussed above have been cited by Lakowicz, who estimates the emission harvest efficiency can still be up to 60% under the averaged results.

Ultimately, these previous studies indicate that the presence of metal should be able to enhance the fluorescence as long as the separation of the fluorophores and metal surface is well controlled. Several other experimental works have successfully demonstrated this capability.

As can be seen from the above discussions, the SPCE phenomenon has significant potential for harvesting and sensing spontaneous emission processes, particularly fluorescence emissions, with extraordinary SNR. While SPCE techniques offer some advantages, there is still a need for a compact optical collection system to collect the wide-angle emission produce by SPCE. It is to such a system and method that the present invention is directed.

DETAILED DESCRIPTION OF THE INVENTION

Figure 1:
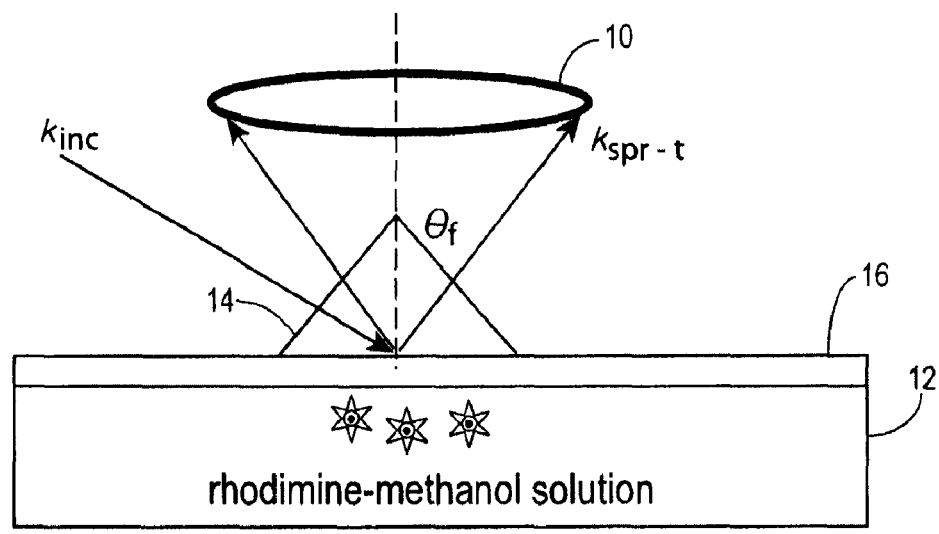
FIG. 1 shows a prior art experimental setup of surface plasmon-coupled emission (SPCE).
Figure 2:
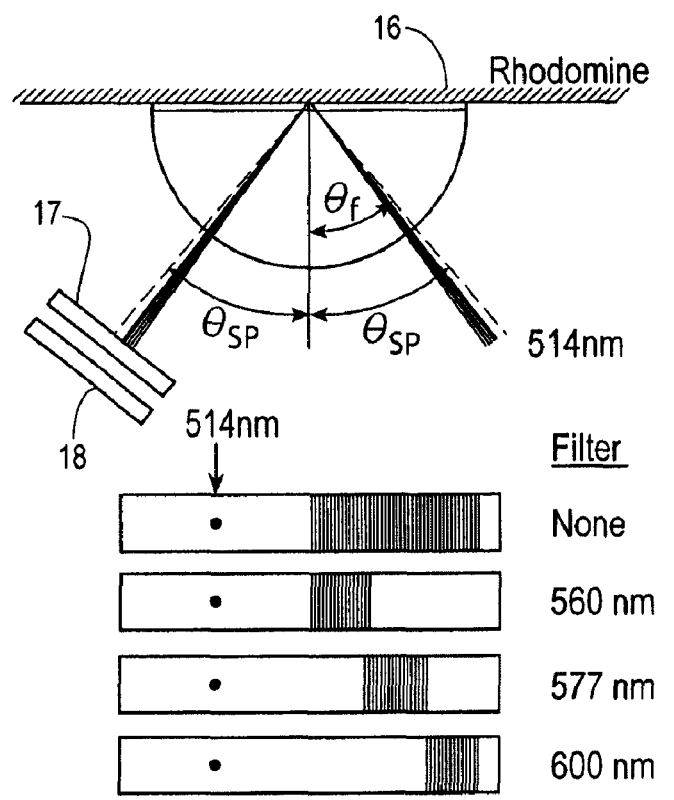
FIG. 2 shows experimental results of the SPCE of FIG. 1.
Figure 3:
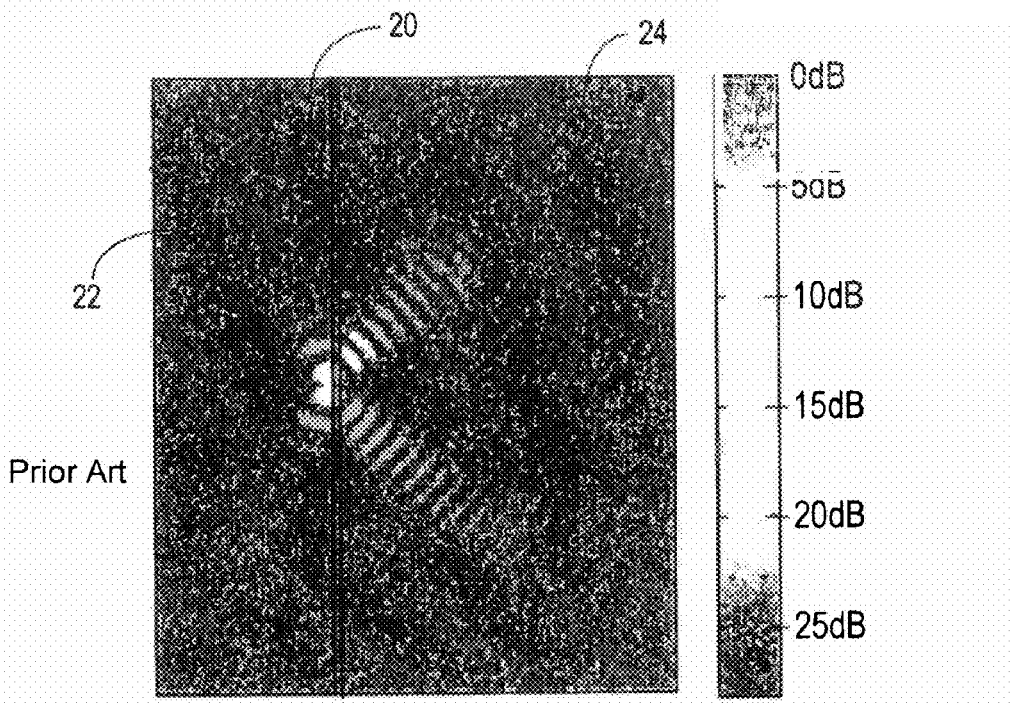
FIG. 3 shows a dipole field coupled into SPCE.
Figure 4:
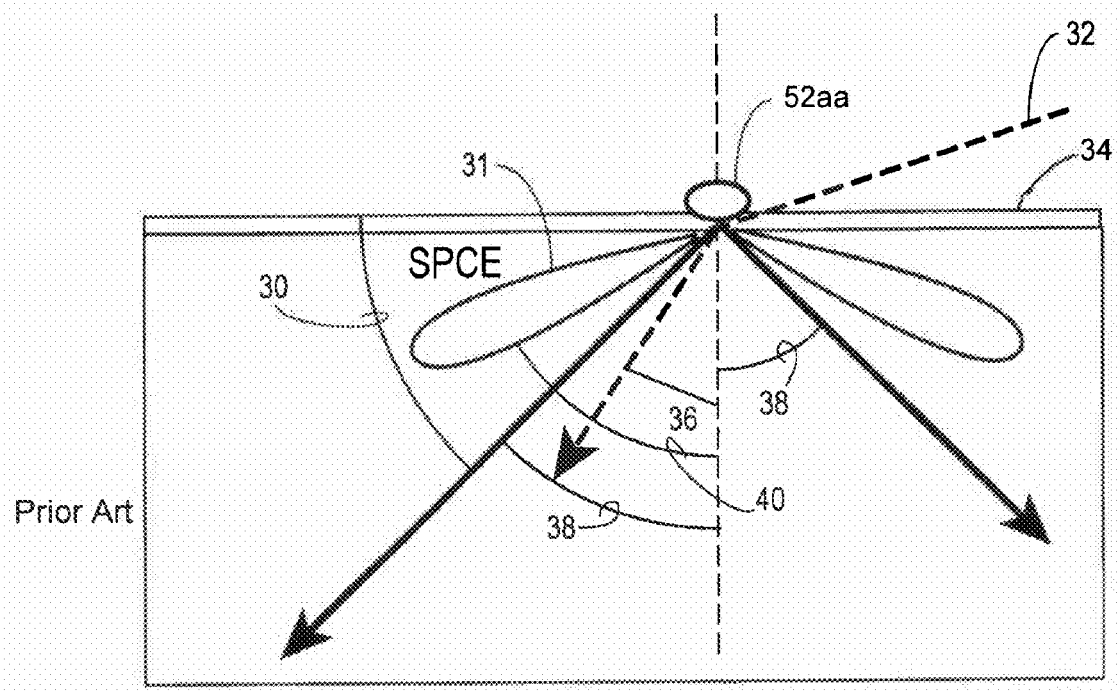
FIG. 4 shows a forbidden light region and radiation pattern of SPCE in a numerical simulation.
Figure 5:
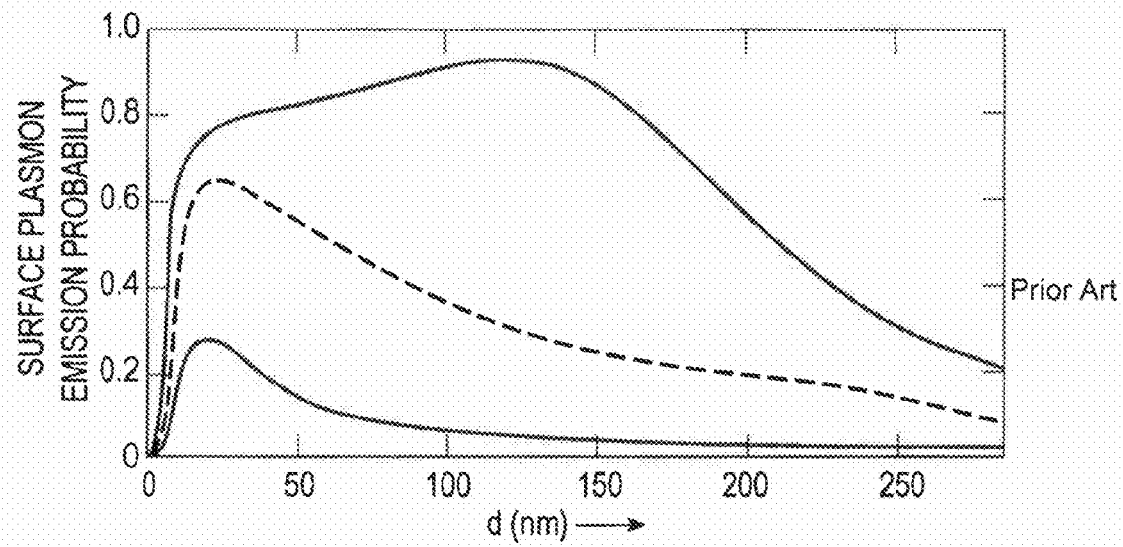
FIG. 5 shows the calculated probability of surface plasmon (SP) emission of an Ag film. The conditions are $\epsilon_s=1.766$, $\epsilon_m=-15.5+i0.5$, $2=600_{nM}$, and Q.E.=1.
Figure 6:
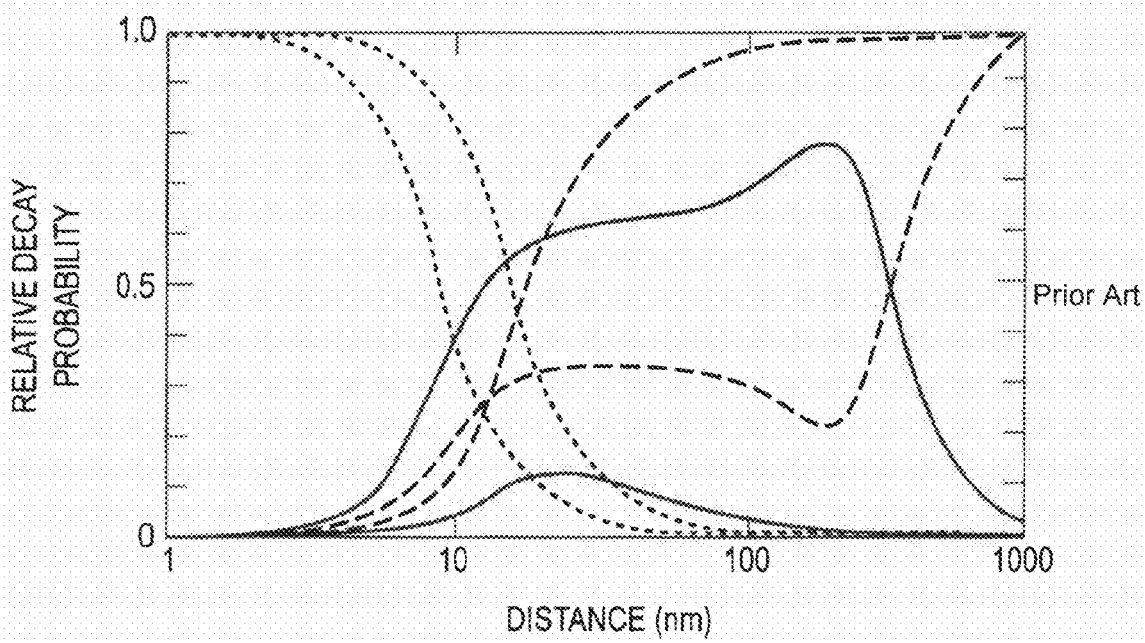
FIG. 6 shows the relative decay probability of both non-radiative and radiative mechanisms.
Figure 7:
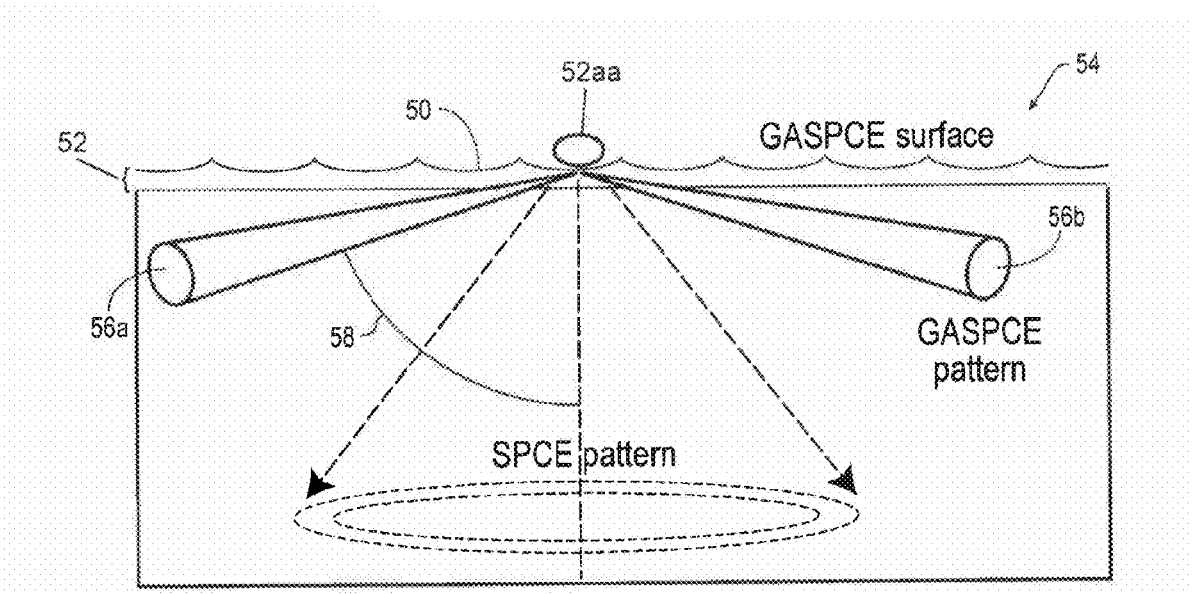
FIG. 7 shows an emission pattern of a grating-assisted surface plasmon-coupled emission (GASPCE).
Figure 7A:
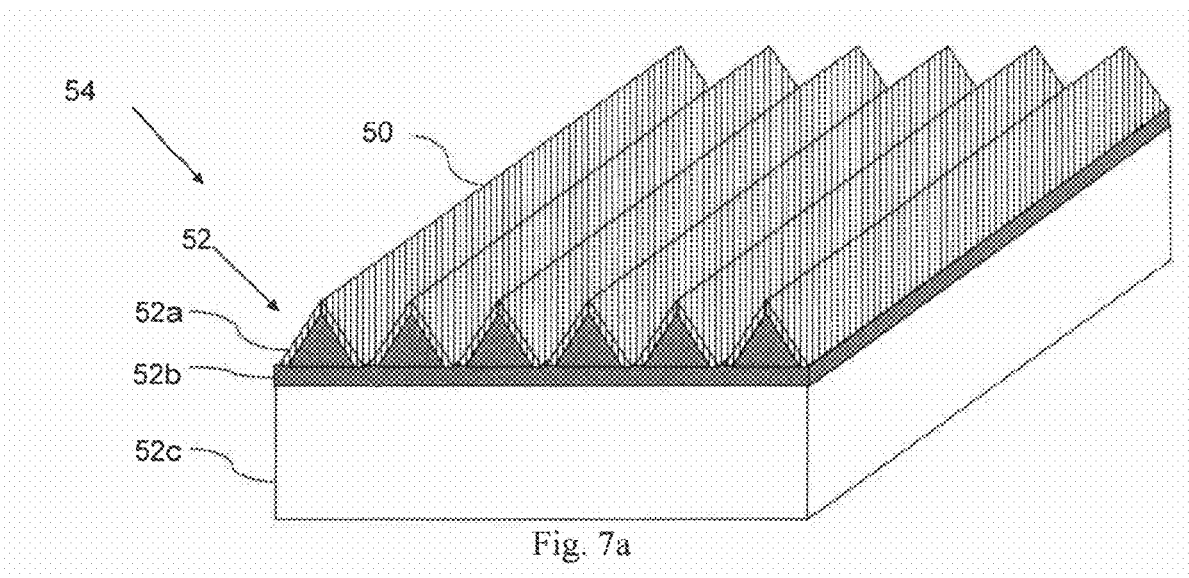
FIG. 7a is a diagram showing the SPCE structure constructed in accordance with the present invention.

Broadly, the present invention relates to improvements in surface plasmon-coupled emission (SPCE) sensing. More particularly, referring to FIG. 7, the present invention allows more efficient collection of a wide-angle emission, such as a spontaneously emitted fluorescent signal via the SPCE, by incorporating a grating structure 50 with an SPCE structure 52 to provide a grating-assisted surface plasmon-coupled emission (GASPCE) system 54. The GASPCE system 54 is further illustrated with reference to FIG. 7a. which shows the grating structure 50 along with the SPCE structure 52, as illustrated by its structural elements of an emitting material 52a, an electrically conductive, light penetrable layer 52b and a substrate layer 52c. Further, an emitter 52aa of the emitting material 52a is illustrated in FIG.7 (see also FIG. 8). The grating structure 50 of the present invention enhances the emission pattern of the SPCE structure 52 so as to provide additional confinement (in both the polar and azimuthal directions) of the emission. As such, the GASPCE system 54 can have a "two beam" distribution 56a and 56b, as shown in FIG. 7, and facilitate coupling of emitted light signals into waveguiding structures, such as optical fibers. Such features of the present invention allows for higher signal collection efficiency, achieving ultra-high SNR, reduced cost in the collection optics and/or detector dimension requirements, compact and robust packaging, and fiber optic sensing applications.

For such an unusual wide-angle emission generally associated with SPCE, common approaches include using mirrors, large numerical aperture optics, or total-internal-reflection-based optics. The optical alignment, excessive optical loss, scattering-induced stray light, and optical surface quality maintenance of those methods are troublesome and problematic for the practical implementation of SPCE. Instead of trying to capture the SPCE with complex optical designs, the present invention utilizes the grating-assisted SPCE (GASPCE) configuration to further enlarge the already wide SPCE emission angle to almost a grazing angle 58 (i.e., where the transmission angle is close to 90°), as shown for example in FIG. 7. The resulting grazing-angle emission beams can be coupled into waveguiding structures conveniently and efficiently. The coupling of the GASPCE and the waveguiding structures has several significant advantages. First, optical waveguides can be designed to allow only certain guiding modes to propagate inside the waveguide channels with minimum loss. The non-propagating mode, which can be imagined as the light bouncing inside the waveguide with wrong angles, will experience significant loss and quickly die out in the channel.

Figure 8:
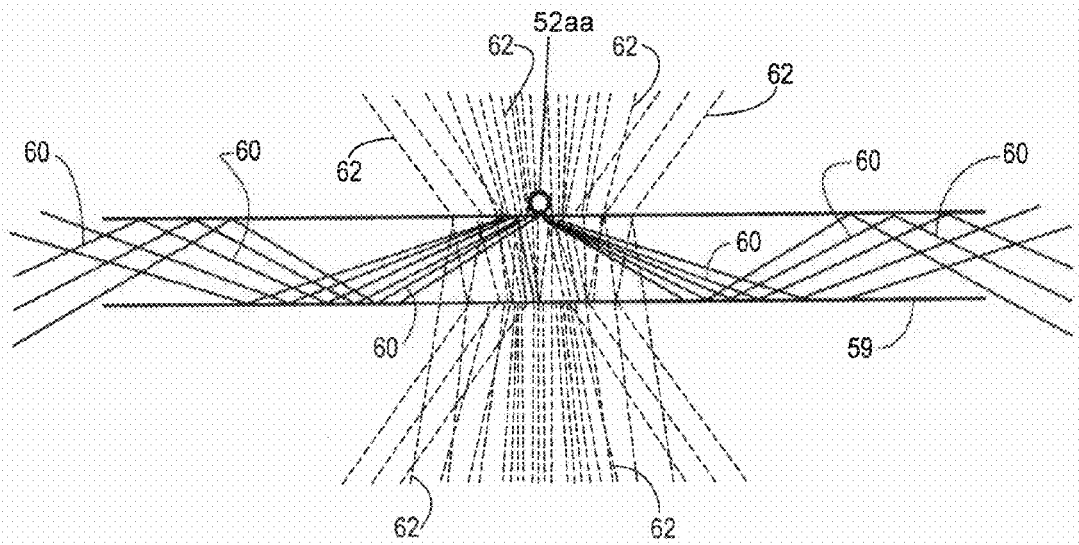
FIG. 8 shows a coupling of the GASPCE and a waveguiding structure.

Shown in FIG. 8 is the coupling of the GASPCE and a waveguide 59, illustrated via ray tracing. The solid lines 60 indicate the GASPCE in the forbidden light region, which is trapped and propagating along the waveguide 59 with low loss. The dashed lines 62 indicate the non-GASPCE light, which enters into the waveguide 59 with an angle smaller than the critical angle and hence experience significant loss in the waveguide.

Optical waveguide technologies, such as optical fibers, have been mature in the industry. The optical quality of the core/cladding interface is so high that the background noise due to the scattering can be minimized and the purity of the forbidden light (i.e., the GASPCE) can be well maintained.

Further, because gratings are an established and accepted technology, the present invention can be readily implemented and easily commercialized. For example, traditional grating SPR platforms have been widely accepted due to their flexibility. Prior art, such as Kitson et al., have presented work to assist grating design for surface plasmon wave (SPW) excitation. Commercial products, such as the FLEX CHIP from HTS Biosystems, are readily available in the market. Also, disposable grating SPR sensing plates have also been proposed and there is significant interest in grating-assisted SPW.

Figure 9:
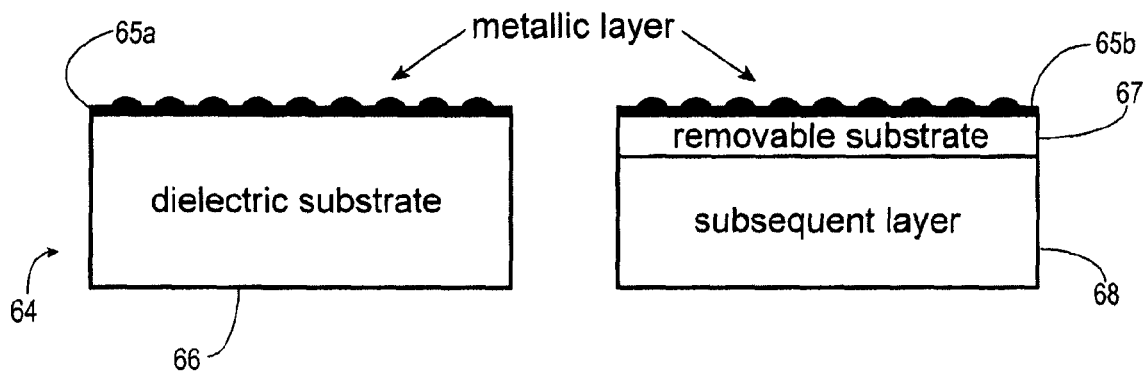
FIG. 9 is an SPCE structure constructed in accordance with the present invention.

Referring to FIG. 9, in one embodiment of the present invention, an SPCE structure 64 of the GASPCE system includes a metal layer 65 (shown as 65a and 65b) and a substrate layer 66.

The metal layer 65a of the SPCE structure 64 can be for example silver, gold, aluminum film, or any metallic film that is capable of supporting surface plasmon resonance. The substrate layer 66 of the SPCE structure 64 is a transparent dielectric medium, such as glass material, polymer material, or silica. The metal layer 65a may be directly deposited on a permanent substrate 66, or the metal layer 65b may be deposited on a removable substrate 67 and then optically attached to a subsequent optical surface 68 so that the SPCE surface may be easily renewed.

The grating structure of the GASPCE system of the present invention can be implemented in various ways. For example, the grating structure may be formed 1) on the metal layer of the SPCE structure, 2) on a substrate layer and then transferred to the metal layer of the SPCE structure, or 3) via a refractive index perturbation in the substrate layer of the SPCE structure. Although the present invention is described as including a grating structure, it should be understood that any periodic photonic structure at the proximity of the emitter and the metallic layer that alters the light propagation mode may be used for the GASPCE system in accordance with the present invention.

Traditionally, gratings have been used in SPR sensing to facilitate the excitation of the surface plasmon wave (SPW) from the free-space side. Since the wavevector of the SPW is always greater than the incident wavevector, it is impossible to excite the SPW at a planar metal surface from the free-space side. The presence of a grating modifies the phase matching criteria so that excitation of SPW from free-space side is possible.

Figure 10:
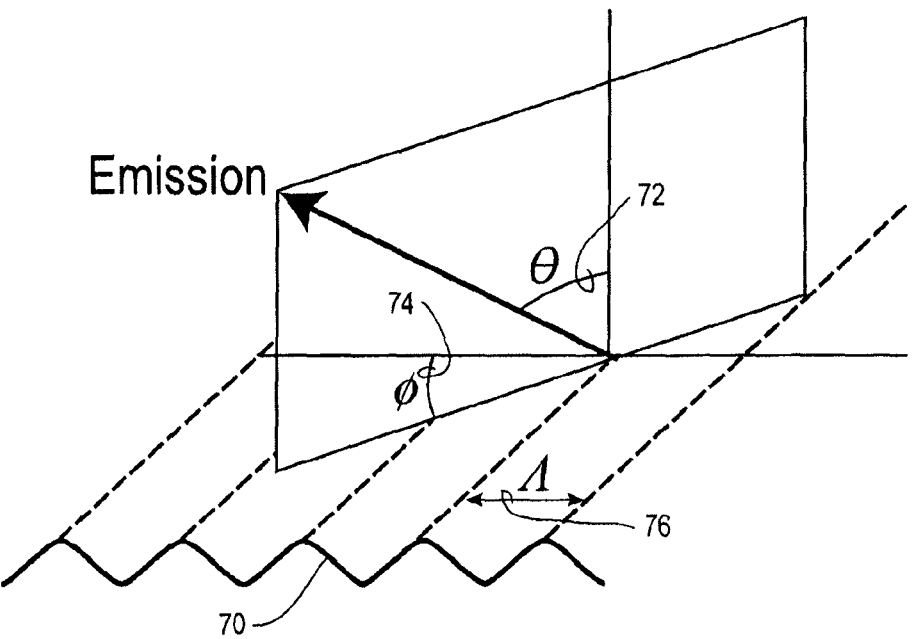
FIG. 10 shows an embodiment of an orientation of gratings.
Figure 10A:
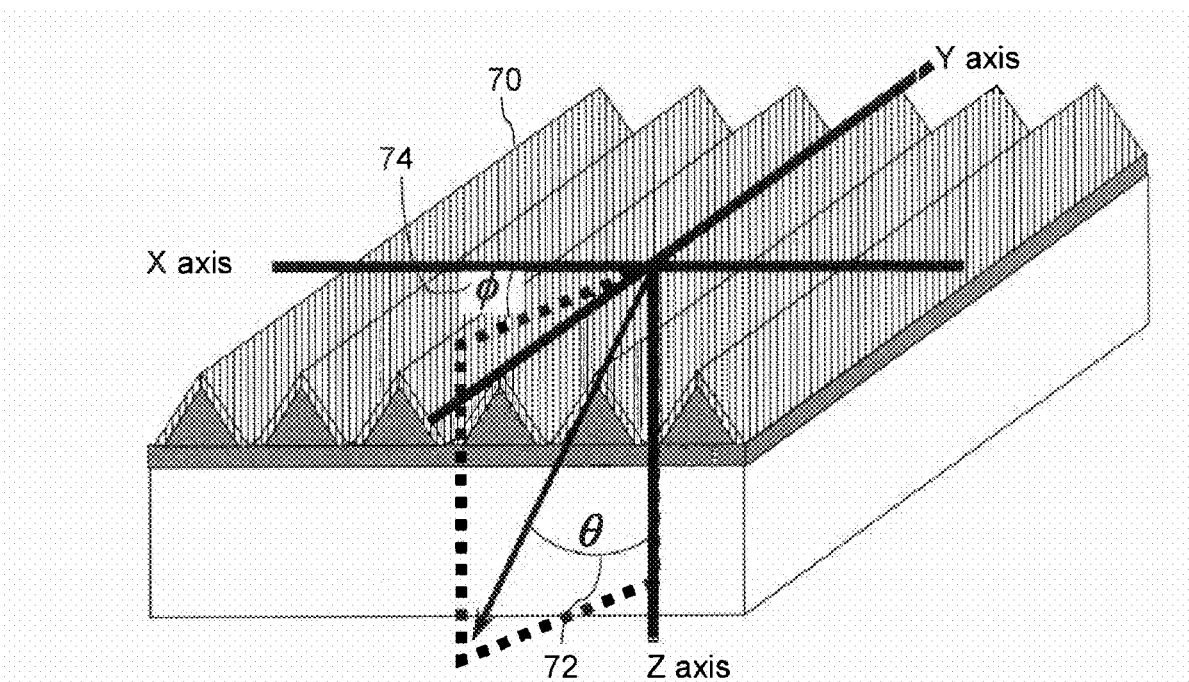
FIG. 10a shows an embodiment of an orientation of gratings with reference to the Cartesian coordinate system and definition of polar ($\theta$) and azimuthal ($\phi$) angles.
Figure 10B:
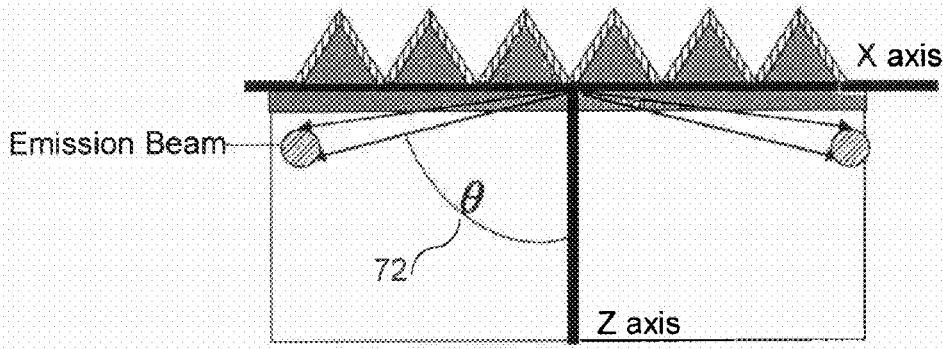
FIG. 10b shows an embodiment of an orientation of gratings and two emission beams with reference to the Cartesian coordinate system from a second perspective.

In the present invention, referring to FIG. 10, the presence of gratings has two effects. First, the grating structure 70 breaks the symmetry in the azimuthal direction so that by super-imposing the gratings upon the SPCE structure, additional emission confinement in the azimuthal direction can be achieved. This means that the GASPCE will emit toward the specific azimuthal 74 (φ) angle in addition to the original polar 72 angle confinement. Secondly, the grating further enlarges the polar emission angle. With these two modifications, the coupling of GASPCE to waveguiding structure is feasible.

Figure 10C:
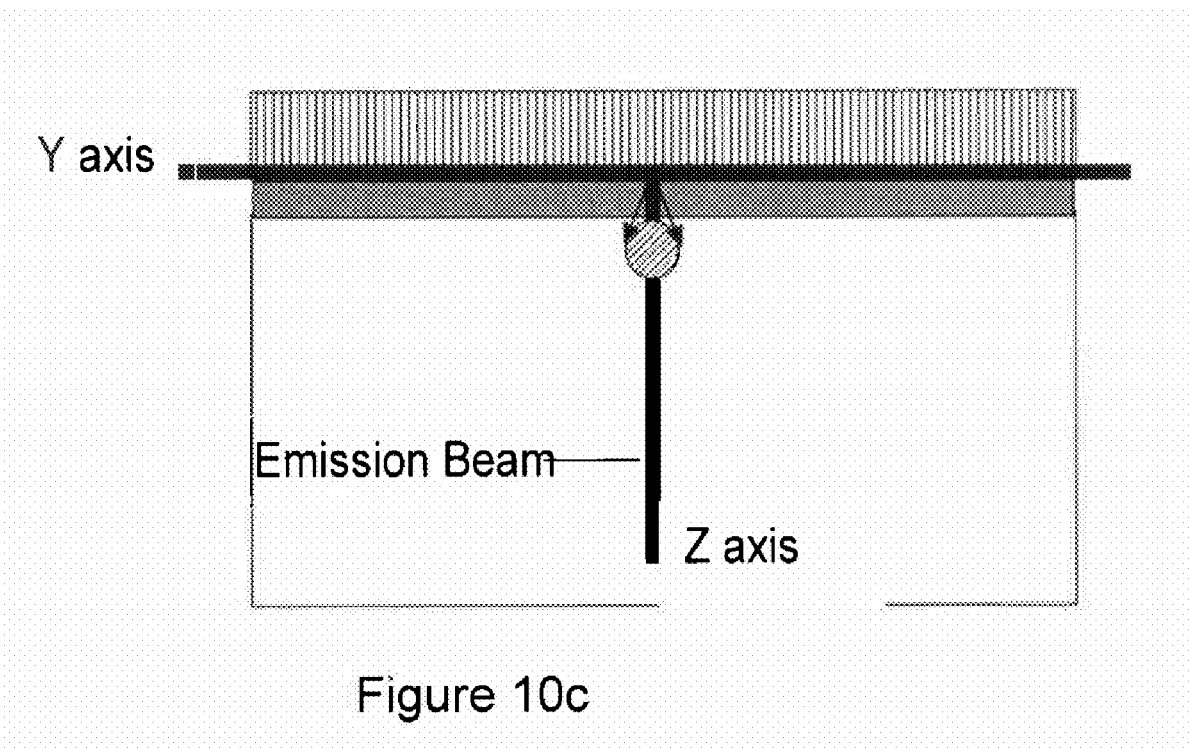
FIG. 10c shoes an embodiment of an orientation of gratings and two emission beams with reference to the Cartesian coordinate system from a third perspective.

The three-dimensional coordinate system related to the GASPCE system 54 is further defined with reference to FIGS. 10-10c. In the Cartesian coordinate system, the X, Y and Z coordinates are used to describe a location. In the present application, the Z axis is perpendicular to the SPCE structure 52 of FIG. 7. The X axis is perpendicular to the grooves of the grating structure 50. For GASPCE emission, it is more convenient to use the spherical coordinate system to specify the spatial distribution with radial distance, polar angle 72 and azimuthal angle 74. Thus, the polar angle θ 72 is defined with respect to the Z axis and the azimuthal angle φ 74 is defined with respect to the X axis.

The GASPCE system 52 constructed in accordance with the present invention not only specifies the polar angle 72 but also the azimuthal angle 74 of the emission due to the presence of the additional requirement of the grating period which is discussed below. Due to the additional design of the grating structure 50, the GASPCE emission light will be directed into a specific polar angle 72 and a pair of azimuthal angles 74 (see also FIG. 7). Therefore, it is termed two-dimensional confinement.

The theoretical background of GASPCE is discussed below with reference to the grating orientation and notations noted in FIG. 10. The grating-modified phase matching criterion among the wavevectors of incident field, SPW, and grating are as follows:

$$k_{gaspce}\sin\theta = \pm k_{spw} \pm nG, \quad k_{gaspce} = \frac{2\pi}{N\gamma_{gaspce}}, \quad G = \frac{2\pi}{\Lambda}, \quad (1)$$

and n is an arbitrary integer; where $k_{gaspce}$, $k_{spw}$, and G are wavevectors for the SPCE field, SPW field, and grating respectively; $\lambda_{gaspce}$ and $\Lambda$ are the SPCE wavelength and the grating period 76 respectively; and N is the refractive index of the substrate.

Figure 11:
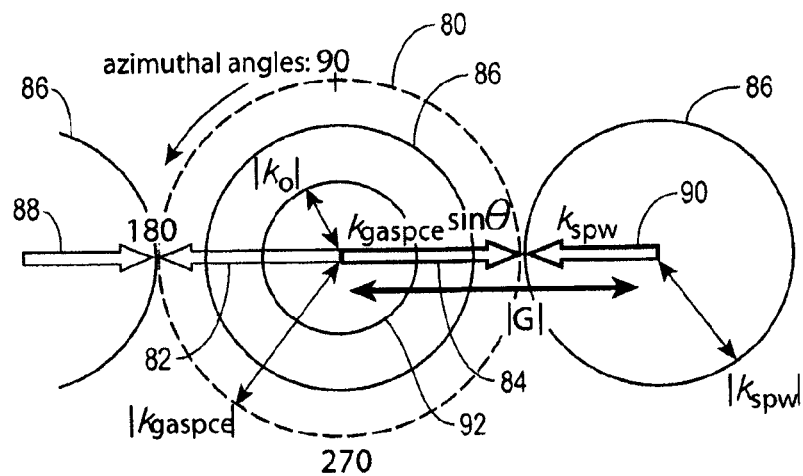
FIG. 11 shows a GASPCE phase matching map.

Equation (1) can be visualized in the phase matching map as it is shown in FIG. 11. In previous studies, the interest was on exciting SPW from the free-space side. In the present invention, a similar analysis is extended to address the GASPCE phenomena. In FIG. 11, the doted circular region 80 indicates the possible distribution of the wavevector of $k_{gaspce} \sin\theta$, wherein two specific wavevectors have been shown as block arrows 82 and 84. Similarly, the circular region 86 and block arrows 88 and 90 stand for the possible distribution and two specific wavevectors of $k_{spw}$. The circular region 92 with smallest radius is the distributing zone of the free space wavevector, $k_o \sin\theta$. The intersection point(s) of the doted circles 80 and the solid circles 86 specify the satisfied phase matching condition(s) to allow GASPCE. FIG. 11 demonstrates one satisfied GASPCE condition located at the intersection of doted circles 80 and the solid circles 86 where the emission polar angle is 90° (i.e., $\sin\theta=1$) and the azimuthal angle ($\phi$) is 0° and 180° with a grating period requirement of $$\Lambda = \frac{2\pi}{k_{gaspce}+k_{spw}} \text{ (i.e., } k_{gaspce}+k_{spw} = G\text{)}.$$

By choosing the grating wavevector (G) large enough (i.e., the grating period small enough), there is no intersection of circles 92 and circles 86 possible so that emission to the free-space is prohibited and all the GASPCE is toward the high refractive index substrate (with the GASPCE wavevectors represented by the block arrows 82 and 84).

As such, the GASPCE of the present invention creates a two-dimensional emission confinement in both polar and azimuthal direction over the original SPCE. Such capabilities provide the following advantages:

- Facilitating the coupling of SPCE-related spontaneous emission into waveguiding structures (e.g., fiber optics) for signal collection.
- Enabling array sensing for multi-target or high throughput detection and remote/distributed detection schemes.
- Further improving the signal-to-noise ratio via propagation mode limitation of the waveguide coupling.
- Allowing the sensor to be packaged in a rug and miniaturized form by reducing the moving parts and eliminating optical alignments.

To demonstrate various embodiments and uses of the present invention, the following examples of are set forth hereinafter. It is to be understood that the examples are for illustrative purposes only and are not to be construed as limiting the scope of the invention as described herein. The invention is capable of other embodiments, or of being practiced or carried out in various ways.

EXAMPLE 1

Figure 12:
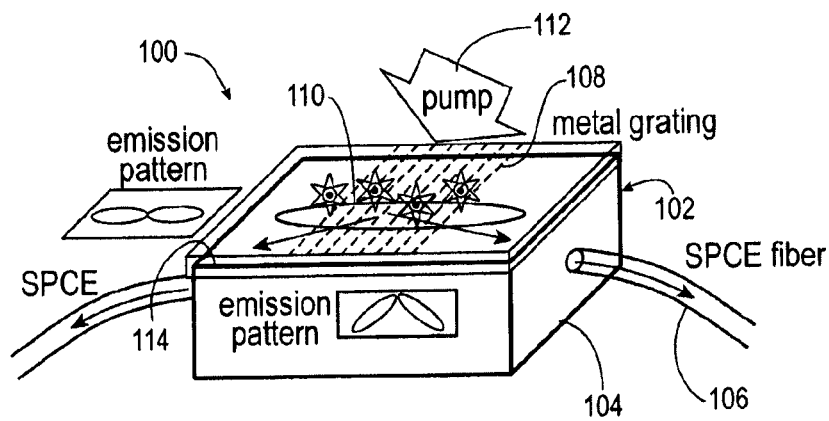
FIG. 12 shows GASPCE collection using an evanescent-wave coupling block.

In one embodiment, as shown in FIG. 12, a GASPCE system 100 of the present invention includes an evanescent wave block 102 which has a glass block 104 with a standard optical fiber 106 running though and immobilized inside the glass block 104. The fiber 106 is bent with a radius of curvature so that some controlled erosion and polishing of the top surface of the fiber 106 exposes the fiber core or cladding for light coupling. The evanescent wave block 102 provides a flat surface to allow (1) the guided light to interact with an ambient material disposed on the evanescent wave block and (2) the GASPCE to be coupled into the optical fiber. The evanescent block 102 includes a combination of a metal grating 108 and a coupling facet 110 to achieve GASPCE collection. The coupling facet 110 includes a light emitter layer (e.g., a fluorescing polymer), a metal layer, and a substrate block or layer. The light emitter layer and metal layer may be directly deposited on the substrate block 102. In an alternative embodiment, the light emitter layer and the metal layer can be deposited on a transparent glass or plastic slide and then the slide can be attached to the substrate block via index matching fluid. For example, the glass or plastic slide with the grating structure engraved on top of it can have a metal coating and a fluorescence reporter. In one embodiment, the glass or plastic slide is disposable, which provides a cost-effective way to renew the sensor.

An excitation light (pump) 112 may be provided either from outside of the block 102 or from inside of block 102 through the optical fiber 106. FIG. 12 shows the configuration with the excitation from the topside 114 of the block 102. The GASPCE is coupled into the optical fiber 106 propagating both directions, which may be merged and sent to the detector. In this first configuration, the excitation light is blocked with a high isolation ratio due to the forbidden light principle. The expected result is an extraordinary fluorescence signal-to-noise ratio.

As discussed above, the excitation light may also be delivered to the sensing facet 110 via the optical fiber 106. In this configuration, the excitation of surface plasmon resonance (SPR) at the incident wavelength is possible since the light is incident from the higher refractive index side. When SPR is generated, the incident field can be amplified and the fluorescence signal strength is further enhanced. The incident light will also be absorbed almost completely at the SPR condition and the contamination to the signal can be minimized. Further, a remote distributed sensing network or parallelized array sensing can be facilitated when both excitation and the generated signal is transported inside the same waveguide. When multiple sensors are used, as discussed further below, various multiplexing schemes can be readily adopted from the telecommunication industry to address each individual sensor in the sensing network.

EXAMPLE 2

Figure 13:
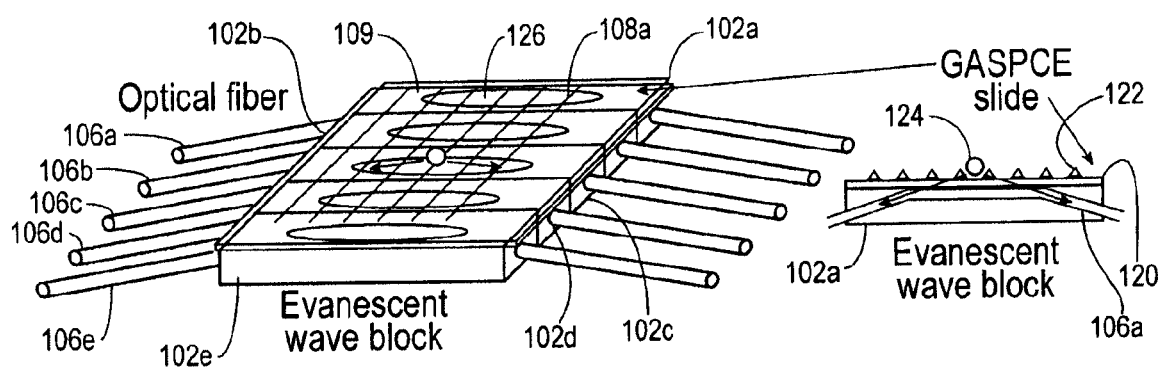
FIG. 13 shows an array GASPCE sensing platform using an evanescent-wave block.

For array sensing applications, a plurality of the evanescent-wave blocks 102a-102e described above in Example 1 can be grouped together, as shown for example in FIG. 13. In this configuration, different reporters (e.g., fluorescence reporters) may be used to form the light signal emitter layers for different channels. The various reporters and the GASPCE grating 108a and metal layers 109 may be directly deposit on the substrate blocks 102a-102e. They may also be deposited on a glass slide 120 with partitions 122 aligned to the different substrate blocks 102a-102e so that various light signals 124 (e.g., fluorescent signals) may go to dedicated waveguide structures 106 via GASPCE.

EXAMPLE 3

Figure 14:
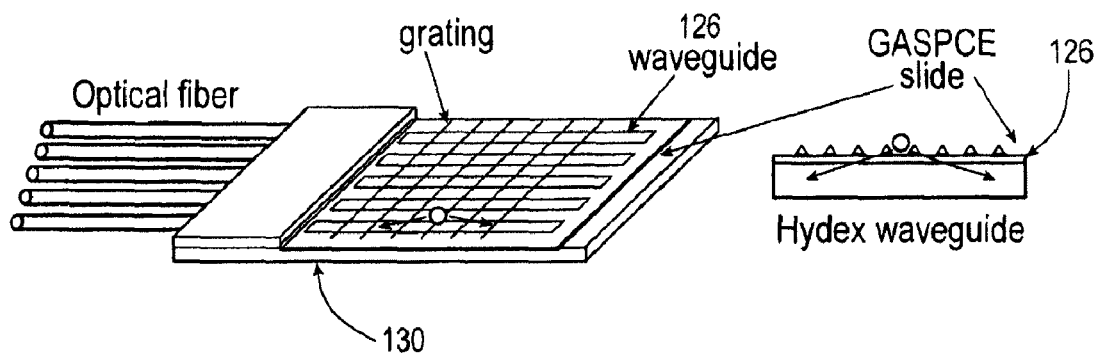
FIG. 14 shows a GASPCE sensing platform using an integrated optical chip.

The integration of the GASPCE system of the present invention with an integrated optical chip enables multi-channel array sensing or high-throughput fluorescence sensing. For example, as shown in FIG. 14, an integrated optics chip 130, such as an optical chip sold under the trademark HYDEX from Little Optics of Annapolis Junction, Md., can be used to form at least one waveguide 126 of the waveguide structure for the collection of GASPCE. Examples for constructing and using the optical chip are described in more detail in U.S. Pat. No. 6,614,977, the entire content of which is hereby incorporated herein by reference.

EXAMPLE 4

As an example of one application of the present invention, the GASPCE-based optical fiber sensor can be incorporated with a vapor sensing instrument taught in U.S. Pat. No. 6,558,626, issued to Aker et. al, the entire contents of which are hereby expressly incorporated herein. In such an example, a detector for detecting vapors emitted from energetic compounds present in a sample can include a housing, a pump, and a sensing assembly. The housing defines an enclosed sensing volume. The housing has an inlet and an outlet communicating with the enclosed sensing volume such that a carrier, such as a gas or fluid, can be moved sequentially through the inlet, the enclosed sensing volume and the outlet. The pump communicates with the housing to move the carrier sequentially through the enclosed sensing volume at a predetermined flow rate. The sensing assembly senses the vapors of the energetic compound delivered by the carrier as the carrier passes through the housing. The sensing assembly includes a sensing unit, a source of excitation, at least one light detector, and a converter assembly.

The sensing unit includes a GASPCE structure disposed in the housing. The GASPCE structure includes a substrate layer, a metal layer disposed on the substrate layer, and a grating structure disposed on the metal layer. The sensing unit also includes a light signal emitter layer comprising an amplifying fluorescent polymer, which is disposed on the GASPCE structure nearby the metal layer of the GASPCE structure. The light signal emitter layer is also positioned on the GASPCE structure so as to be openly communicating with the enclosed sensing volume of the housing. The intensity of light emitted by the amplifying fluorescent polymer will vary in response to interaction of the amplifying fluorescent polymer with molecules of the energetic compound delivered by the carrier.

The source of excitation of the sensing assembly produces a medium that interacts with the light signal emitter layer of the sensing unit to cause the amplifying fluorescent polymer of the light signal emitter layer to generate light. When a light signal is emitted by the amplyifing fluorescent polymer, the light signal travels through the GASPCE-enabling structure, is coupled into the grating-assisted surface plasmon mode, and is reradiated into the previously described GASPCE pattern. The fluorescence light signal is then coupled into a waveguiding structure (e.g., optical fiber) and delivered to a light detector.

The light detector outputs a signal indicative of the intensity of the received portion of the light generated by the amplifying fluorescent polymer. The converter assembly receives the signal from the light detector and converts such signal into a format perceivable by an individual.

EXAMPLE 5

Figure 15:
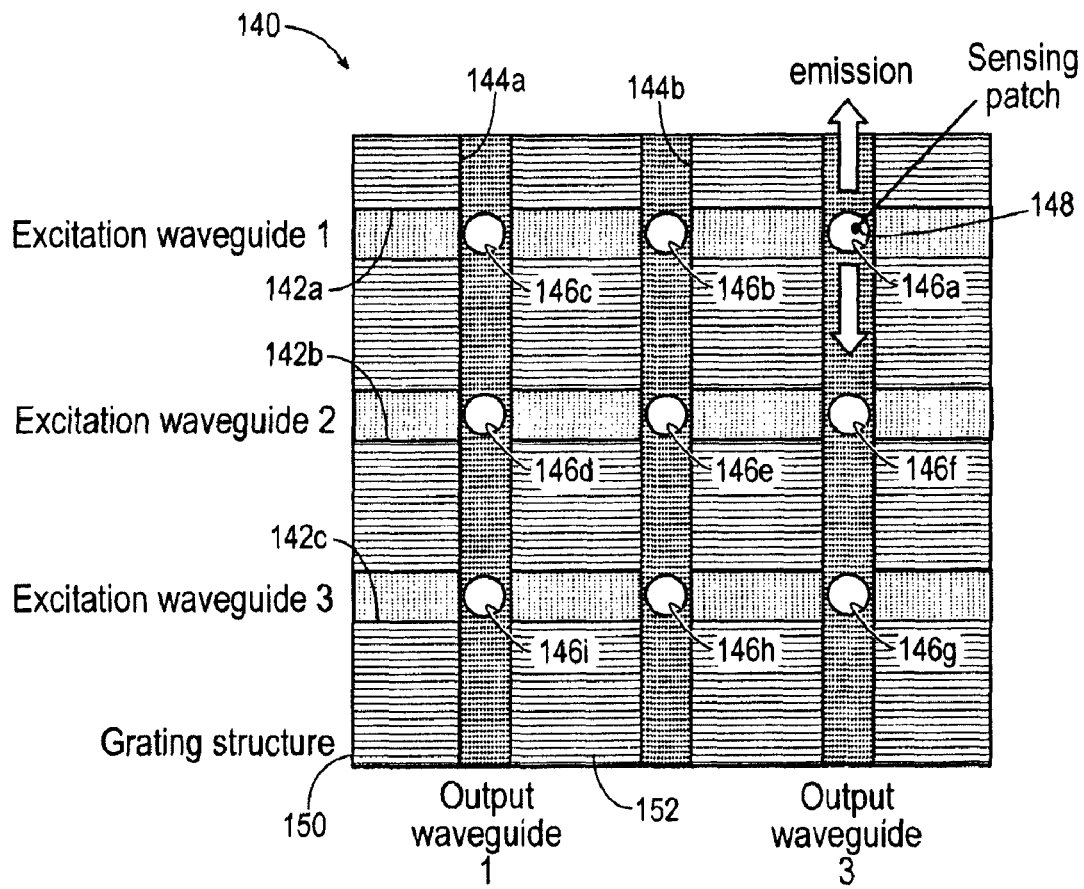
FIG. 15 is an example of a microarray GASPCE substrate constructed in accordance with the present invention.

Traditional microarray fluorescence detection system excites and detects the fluorescence signal from the sample material deposited on a glass substrate. The signal collection efficiency and signal to noise level can be low due to the nature of fluorescence emission distribution. GASPCE scheme can be used as the improved microarray system. The substrate may be an integrated optical chip with waveguiding structure embedded underneath the GASPCE structure. Shown in FIG. 15 is a simple 3×3 microarray GASPCE system 140 where multiple excitation waveguides 142a-142c run horizontally and detection or output waveguides 144a-144c go vertically. Multiple sensing patches 146a-146i are deposited on the intercepting areas of the excitation waveguides 142a-142c and detection waveguides 144a-144c. Each patch 146a-146i has an emitting material 148 deposited on the GASPCE layered. The grating structure 150 for GASPCE has grooves 152 run along with the excitation waveguide 142 so that the emission is coupled into the output waveguide 144 running vertically.

Although the foregoing invention has been described in some detail by way of illustration and example for purposes of clarity of understanding, it will be apparent to those skilled in the art that certain changes and modifications may be practiced without departing from the spirit and scope thereof, as described herein. Also, it is to be understood that the phraseology and terminology employed herein is for purpose of description and should not be regarded as limiting.

The entire contents of each of the following references are hereby expressly incorporated herein.

REFERENCES

W. H. Weber and C. F. Eagen, "Energy transfer from an excited dye molecule to the surface plasmons of an adjacent metal," Optics Letters, 4, 236, 1979.

G. W. Ford and W. H. Weber, "Electromagnetic interactions of molecules with metal surfaces," Physics Reports, 113, 195, 1984.

J. R. Lakowicz, "Radiative decay engineering 3. Surface plasmon-coupled directional emission," Analytical Biochemistry, 324, 153, 2004.

I. Gryczynski, J. Malicka, Z. Gryczynski, and J. R. Lakowicz, "Radiative decay engineering 4. Experimental studies of surface plasmon-coupled directional emission," Analytical Biochemistry, 324, 170, 2004.

T. Ruckstuhl, J. Enderlein, S. Jung, and S. Seeger, "Forbidden light detection from single molecules", Analytical Chemistry, 72, 2117, 2000.

J. Enderlein, T. Ruckstuhl, and S. Seeger, "Highly efficient optical detection of surface-generated fluorescence," Applied Optics, 38, 724, 1999.

J. Enderlein, "Single-molecule fluorescence near a metal layer," Chemical Physics, 247, 1, 1999.

R. W. Gruhlke and D. G. Hall, "Transmission of molecular fluorescence through a thin metal filem by surface plasmon," Applied Physics Letters, 53, 1041, 1988.

S. C. Kitson, W. L. Barnes, and J. R. Sambles, "Photoluminescence from dye molecules on silver gratings," Optics Communications, 12, 147, 1996.

Electronic Surface Mode, ed. A. D. Boardman, Wiley, New York, 1982. HTS Biosystems, http://www.htsbiosystems.com/products/flex$_{13}$chip.htm.

C. R. Lawrence, N. J. Geddes, and D. N. Furlong, "Surface plasmon resonance studies of immunoreactions utilizing disposable diffraction gratings," Biosensors and Bioelectronics, 11, 389, 1996.

Little Optics, Inc., http://www.littleoptics.com.

What is claimed is:

1. A grating assisted surface plasmon coupled emission system comprising:
    a surface plasmon-coupled emission (SPCE) structure including an emitting material, an electrically conductive, light penetrable layer and a substrate layer wherein the electrically conductive, light penetrable layer is positioned between the emitting material and the substrate layer and supports surface plasmon resonance and the substrate layer is a transparent dielectric medium supporting the electrically conductive, light penetrable layer; and a periodic photonic structure defining a grating having a grating period directing an optical emission from the emitting material into a two-dimensional confinement in the azimuthal and polar directions propagating into the substrate layer.

2. The system of claim 1 wherein the optical emission is fluorescence, Raman scattering, or second harmonic generation.

3. The system of claim 1 wherein the electrically conductive, light penetrable layer is a metal layer.

4. The system of claim 3 wherein the metal layer is silver, gold, or aluminum.

5. The system of claim 1 wherein the substrate layer is a glass or polymer material.

6. The system of claim 1 wherein the periodic photonic structure is a grating structure.

7. The system of claim 6 wherein the grating structure has a uniform periodicity and a groove depth with arbitrary undulated profiles.

8. The system of claim 1 wherein the grating is formed by the electrically conductive, light penetrable layer of the SPCE structure having a corrugated surface.

9. The system of claim 1 wherein the grating is formed by a corrugated surface of the substrate layer.

10. The system of claim 1 wherein the grating is formed via a refractive index perturbation in the substrate layer of the SPCE structure.

11. The system of claim 1 further comprising:
a waveguide structure having a coupling portion positioned about parallel with the substrate layer and receiving the optical emission at a transmission angle to trap the optical emission.

12. The system of claim 1 wherein the substrate layer is an integrated optical chip having a multiple grating-assisted surface plasmon-coupled emission (GASPCE) surface thereon.

13. The system of claim 11, wherein the waveguide structure is an optical fiber.

14. The system of claim 1, wherein the grating period satisfies the condition $\Lambda=2\pi/G$ where $\Lambda$ is the grating period and $G=k_{gaspce}+k_{spw}$ is the sum of the wavevectors of the optical emission coupled into the substrate and a surface plasmon wave induced in the electrically conductive, light penetrable layer.

* * * * *